United States Patent [19]
Kolc et al.

[11] Patent Number: 5,223,252
[45] Date of Patent: Jun. 29, 1993

[54] PERMANENT WAVE COMPOSITION AND METHOD

[75] Inventors: Stanley J. Kolc, Chicago; Richard A. Abbott, Westmont; Arun Nandagiri, Libertyville, all of Ill.

[73] Assignee: Helene Curtis, Inc., Chicago, Ill.

[21] Appl. No.: 919,972

[22] Filed: Jul. 27, 1992

Related U.S. Application Data

[63] Continuation of Ser. No. 670,056, Mar. 15, 1991, abandoned.

[51] Int. Cl.$^5$ ............................................. A61K 7/09
[52] U.S. Cl. ........................................ 424/72; 424/71; 131/203; 131/205
[58] Field of Search ................ 424/72, 71; 132/203, 132/204, 205, 209

[56] References Cited

U.S. PATENT DOCUMENTS

| | | | |
|---|---|---|---|
| 4,272,517 | 6/1981 | Yoneda et al. | 424/72 |
| 4,424,820 | 1/1984 | Cannell et al. | 424/72 X |
| 5,116,608 | 5/1992 | Yoshioka et al. | 424/72 |

FOREIGN PATENT DOCUMENTS

| | | |
|---|---|---|
| 344653 | 12/1989 | European Pat. Off. . |
| 352375 | 1/1990 | European Pat. Off. . |

OTHER PUBLICATIONS

JP 73 14934 B-english abstract.

*Primary Examiner*—Thurman K. Page
*Assistant Examiner*—Neil Levy
*Attorney, Agent, or Firm*—Marshall, O'Toole, Gerstein, Murray & Borun

[57] ABSTRACT

A mild, alkaline permanent wave reducing composition and method of permanently waving or reshaping human hair that provides a strong, long lasting curl like an alkaline permanent wave composition but leaves the hair soft like an acid permanent wave composition and leaves essentially no post-perm odor. The composition contains about 2.0% to about 6.5% by weight of a cysteine reducing agent compound selected from the group consisting of cysteine, a cysteine salt, and mixtures thereof; about 4.5% to about 8.0% of a thioglycolate; and sufficient additional alkali, if necessary, to bring the pH of the composition within the rang of about 7.5 to about 9.5.

20 Claims, No Drawings

PERMANENT WAVE COMPOSITION AND METHOD

This application is a continuation of application Ser. No. 07/670,056, filed Mar. 15, 1991, now abandoned.

FIELD OF THE INVENTION

The present invention is directed to a cysteine-based composition and method for relatively permanently reshaping or curling human hair into a lasting curl pattern. More particularly, the present invention is directed to a composition and method capable of forming a "permanent" wave in human hair including a cysteine reducing agent within a relatively narrow range of about 2.0% to about 6.5% by weight; and a thioglycolate reducing agent within a relatively narrow range of about 4.5% to about 8.0% by weight of the composition to provide a permanent wave composition that has the distinct advantage of no post-perm odor, without sacrificing performance, such as curl formation, curl spring, manageability, ease of combing, body, luster, soft feel, and the like. The composition can be applied to the hair, with or without heating, as a water wrap or a lotion wrap to produce a strong curl while leaving the hair feeling soft like an acid permanent wave composition without odor.

BACKGROUND OF THE INVENTION AND PRIOR ART

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound into a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

There are three general types of permanent wave compositions or lotions used to break the cystine bonds in human hair, generally known as acid wave compositions; alkaline wave compositions; and neutral wave compositions. Of these three, the acid and alkaline wave compositions are most significant commercially. Permanent wave compositions containing an alkaline salt of thioglycolic acid (TG), such as ammonium thioglycolate as the reducing agent, are generally known as alkaline wave compositions and generally have a pH in the range of about 7.5 to about 9.4. The alkaline wave compositions are known as the conventional cold wave compositions, since free alkali penetrates and swells the hair shaft allowing the reducing agent to enter the hair shaft and break the sulfur to sulfur bonds without added heat. The permanent wave compositions containing glycerol monothioglycolate (GMTG) are known as acid wave compositions even though the pH of these compositions can be as high as about 9.0. Generally speaking, the acid permanent wave compositions have a lower pH than the alkaline permanent wave compositions and, therefore, require heat and/or longer processing time to achieve sufficient reaction of the reducing agent. The alkaline permanent wave compositions produce a stronger, longer lasting curl while the acid permanent wave compositions provide a softer feel but a shorter curl duration. The permanent wave compositions containing an alkaline salt of thioglycolic acid and/or glycerol monothioglycolate leave the hair with a very noticeable sulfur odor.

The reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate) form at a pH near neutral, or slightly acidic pH. Hence, the pKa value shows that some mercaptans are efficient at high pH while others with a low pKa value and high ionization constant are efficient at lower pH values. For example, it is well known that the alkaline salts of thioglycolic acid, e.g., the ammonium salt of thioglycolic acid (pKa=10.4) has acceptable waving efficiency only if the pH of solution exceeds 9.0, see Zviak, Charles, The Science of Hair Care, Permanent Waving and Hair Straightening, p. 191, 1986; while amides such as thioglycolamide (pKa=8.4), and esters such as glycerol thioglycolate (pKa=7.8) give acceptable waving efficiency at neutral and even slightly acid pH.

The cysteine and thioglycolate-based reducing agent-containing composition and method of the present invention are unexpectedly effective in the pH range of about 7.5 to about 9.5 and particularly in the pH range of about 9.0 to about 9.5. Compositions having a pH in the lower end of the pH range (e.g., about 7.5 to about 8.5) are most effective for bleached hair, while compositions having a pH in the higher end (e.g., about 9.0 to about 9.5) are most effective for normal and curl-resistant hair. A number of compositions can be provided that are particularly suited for permanent waving hair in different conditions.

For example, a composition for permanently waving normal and tinted hair (hair with little damage) contains about 5.0% to about 7.0% thioglycolate and about 4.0% to about 6.0% cysteine; a composition for bleached hair contains about 3.5% to about 5.5% thioglycolate and about 2.0% to about 4.0% cysteine; and a composition for curl-resistant hair contains about 5.5% to about 7.5% thioglycolate and about 5.0% to about 6.5% cysteine.

Different reducing agents are effective to break the cystine bonds that cross link human hair protein at different pH's. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pH's in the range of about 7.5 to 9.5, require an alkaline salt of thioglycolic acid or an alkaline salt of a dithioglycolic acid—so that the alkali can penetrate and swell the hair shaft for easier penetration of the reducing agent in order to break the sulfur to sulfur cystine bonds.

Perhaps the most difficult factor for the applier of the permanent wave lotion to assess in determining how long to apply the reducing agent to the hair is the condition of the hair at the time of the permanent wave. It is well documented in the literature and prior art that the hair can be damaged by abuse of chemicals, e.g., by shampooing, permanent waving, tinting, frosting, bleaching, and particularly any hair treatment involving the use of hydrogen peroxide; mechanical treatment, e.g., thermal appliances; and environmental conditions, e.g., climate and pollution. It is well known that damaged hair, depending upon the stage and degree of damage of the hair, has significantly different chemical activity to reducing agents than normal or undamaged hair. If too many of the sulfur to sulfur bonds in the hair are broken by the reducing agent, the hair will be seriously weakened and may disintegrate.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, and capable of retaining this shape. If too few of the sulfur to sulfur bonds are broken, the natural or normal configuration of the hair will predominate, causing the hair to retain its previous shape. This is because the predominant prior or natural bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be as strong as the prior or natural cystine hair bonds. It is desired, therefore, when permanent waving, that enough new bonds in a new hair configuration are formed during permanent waving to equal the number of old bonds remaining that tend to form the hair in its prior or natural configuration, whether it be straight or naturally curled.

Generally, the reducing agent lotion is applied to the hair by first shampooing the hair and then applying the reducing agent lotion to the hair, either before or after the hair is wrapped around suitable rollers. When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

In accordance with the present invention, an alkaline permanent wave composition is provided in a single formula capable of being water wrapped with or without the use of a dryer, heating caps or other heat treatment to speed the reducing agent reaction. The composition of the present invention produces a strong curl similar to alkaline wave composition yet leaves the hair feeling soft like an acid wave composition without postperm odor normally associated with thioglycolate-containing, e.g., ammonium thioglycolate-containing permanent wave composition.

Prior art alkaline compositions containing a salt of thioglycolic acid as a reducing agent are known to produce a tight curl but leave the hair feeling harsh due to the high alkalinity content. Such compositions, however, produce a distinct post-perm sulfur odor, even if used with cysteine, due to the presence of too high a concentration of ammonium thioglycolate; or such compositions have a low perm efficacy. Prior art acid wave compositions containing glycerol monothioglycolate also leave the hair with a strong sulfur odor. Acid wave compositions generally require heat to help swell the hair for reaction with the reducing agent since the hair is not normally swelled sufficiently at the low pH of the acid wave compositions. The cysteine, thioglycolate-based reducing agent-containing permanent wave compositions of the present invention solve the above mentioned prior art deficiencies without causing a post-perm odor, even immediately after the permanent wave composition is applied.

SUMMARY OF THE INVENTION

In brief, the present invention is directed to a mild, alkaline permanent wave reducing composition and method of permanently waving or reshaping human hair that provides a strong, long lasting curl similar to alkaline permanent wave composition but leaves the hair soft like an acid permanent wave composition, without a post-perm odor. Generally, the composition contains a cysteine reducing agent (2-amino-3-mercaptopropionic acid) compound selected from the group consisting of cysteine, a cysteine salt, e.g., cysteine hydrochloride, and mixtures thereof; a monothioglycolate, e.g., ammonium thioglycolate or monothioglycolic acid ester, e.g., thioglycerol.

The cysteine compound should be present in an amount of about 2.0% to about 6.5% by weight; generally about 4.0% to about 6.0%, and preferably about 5.0% by weight for normal or tinted (not substantially damaged) hair; generally about 2.0% to about 4.0%, preferably about 2.0% to about 3.0% cysteine for bleached hair; and generally about 5.0% to about 6.5% cysteine, preferably about 6.0% for curl-resistant hair. Similarly, the amount of thioglycolate can be varied to best suit the condition of the hair being permanently waved. The thioglycolate should be present in an amount of about 4.5% to about 8.0% by weight, generally about 5.0% to about 7.0%, preferably about 6.0% by weight thioglycolate for normal or tinted hair; about 3.5% to about 5.5%, preferably about 4.5% by weight thioglycolate for bleached hair; and about 5.5% to about 8.0%, preferably about 6.5% by weight thioglycolate for curl-resistant hair; and sufficient additional alkali, if necessary, to bring the pH of the composition to within the range of about 7.5 to about 9.5. Optionally, a hair softening and/or moisturizing agent, such as glycerine is included in the composition in an amount of about 0.1% to about 20% by weight, preferably about 0.1% to about 15% by weight of the composition. Optionally, one or more conditioning agents, such as a silicone oil and/or silicone gum; and/or a quaternary conditioning agent also is included in the composition for conditioning benefits and hair shine in an amount of about 0.1% to about 20% by weight of the composition. Fragrances and other common additives also can be included in the usual amounts of about 0.1% to about 5.0% by weight of the composition. This composition is easy to use and apply without significantly damaging the hair while providing a strong, tight curl and leaving the hair unexpectedly soft. Quite surprisingly, the composition leaves no noticeable post-perm odor. The composition can be lotion or water wrapped and can be used with or without heat.

Accordingly, an aspect of the present invention is to provide a new and improved permanent wave composition capable of breaking sulfur to sulfur bonds in human hair so that the hair can be reconfigured in a different configuration. The sulfur to sulfur human hair bonds can be reestablished with an oxidizing agent to maintain the new hair configuration for a substantial time period.

Another aspect of the present invention is to provide a new and improved permanent wave lotion containing a combination of cysteine and thioglycolate reducing agents, in specific amounts, capable of effectively breaking sulfur to sulfur hair bonds without noticeable post-perm odor.

Another optional aspect of the present invention is to provide a permanent wave reducing agent-containing composition including a hair softening and moisturizing agent that enhances the softness and shine achieved with the composition and without leaving a noticeable odor in the hair.

These and other aspects and advantages of the present invention will become apparent from the following detailed description of the preferred embodiment.

DETAILED DESCRIPTION OF THE PREFERRED EMBODIMENT

The present invention is directed to a cysteine, thioglycolate-based permanent wave composition capable of permanently waving hair, using either a water-wrap or a lotion wrap, applied as a mild alkaline permanent which unexpectedly leaves the hair feeling soft like an acid wave, yet produces a tight, long lasting curl formation similar to that of an alkaline wave but without post-perm odor. The capability of permanently waving hair using a cysteine, thioglycolate-based, reducing agent composition without leaving a post-perm odor is unique in the industry.

The composition of the present invention is a mild, alkaline permanent wave conditioning composition capable of waving or reshaping human hair and provides a strong, long lasting curl similar to an alkaline permanent wave composition while leaving the hair soft like an acid permanent wave composition without a post-perm odor. Generally, the composition contains a cysteine compound selected from the group consisting of cysteine, a cysteine salt, and mixtures in an amount of about 2.0% to about 6.5% by weight, and a thioglycolate in an amount of about 4.5% to about 8.0%.

The reducing agent composition of the present invention has a pH in the range of about 7.5 to about 9.5. A pH within the desired range, depending upon the type of hair being permanently waved, can be achieved by the addition of an alkanolamine, ammonia, an ammonium carbonate, and/or a metal hydroxide to the composition of the present invention. Optionally, the reducing composition also includes a hair moisturizer and/or softener selected from a polyhydroxyl alkyl compound, a polyalkylene glycol glycerol ether, an ethoxylated fatty alcohol, a fatty alcohol polyglycol ether, and mixtures thereof in an amount of about 0.1% to about 20% by weight, particularly about 0.1% to about 15% by weight.

In accordance with one optional embodiment of the present invention, the composition of the present invention also includes from about 0.1% to about 10%, particularly about 0.5% to about 10%, and preferably from about 1.0% to about 5.0%, by weight of a non-volatile silicone compound or other conditioning agent(s), such as polymeric quaternary ammonium salts, preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g., 700,000 centistokes plus, and a weight average molecular weight of at least about 500,000 also are useful in accordance with the present invention.

Preferred silicone gums include linear and branched polydimethylsiloxanes, of the following general formula:

wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agent.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structure formula (I), wherein n ranges from 2 to 5,

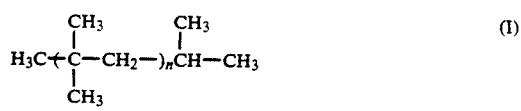

Examples of volatile hydrocarbons useful in the composition of the present invention are the commercially-available compounds PERMETHYL 99A and PERMETHYL 101A, corresponding to compounds of general structure (I), wherein n is 2 and 3, respectively, available from Permethyl Corporation, Frazer, Pa. A volatile hydrocarbon compound is useful in the composition of the present invention either alone, in combination with another volatile hydrocarbon, or in combination with a volatile silicone.

Examples of other suitable water-insoluble conditioning agents that can be incorporated into the permanent wave compositions include the polymeric quaternary ammonium salts, such as Polyquaternium 1 through Polyquaternium 14, inclusive, and any combination of such conditioners, as defined on page 245, CTFA Cosmetic Ingredient Dictionary, Third Edition, 1982, hereby incorporated by reference. The preferred conditioners are Polyquaternium-4, Polyquaternium-10, and Polyquaternium-11. The conditioner, when added, is included in an amount of about 0.01% to about 2.0% by weight of the composition.

Other common cosmetic additives can be incorporated into the composition of the present invention, as long as the basic properties of the permanent wave composition are not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols such as ethanol and isopropanol and mixtures. These solvents can be present in the hair setting composition of the present invention in an amount from about 1% to about 75% by weight and in particular from about 5% to about 50% by weight, based on the total weight of the composition.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as polymers of acrylic acid or polymeric acrylic acid derivatives. It is also possible to use inorganic thickeners such as bentonite. These thickeners, when included, preferably are present in an amount from about 0.1% to about 10% by weight and, in particular, from about 0.5% to about 3% by weight, based on the total weight of the composition.

The optional use of polyhydric alcohols or polyhydroxy alkane compounds, such as ethylene glycol, glycerine, propylene glycol, or polyoxyethylene glyceryl ethers in this composition leaves the hair in better condition due to humectant properties and provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3-butylene glycol, 1,2,6-hexanetriol, 1,5-pentanediol, 2-ethyl pentanediol-2,4, and 2-ethyl hexanediol-1,3. Further examples of suitable moisturizers include the polyalkylene glycols, such as those compounds having the formula

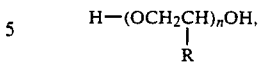

wherein R is H or CH$_3$, and n has an average value of 2 to 600; when R=H, particularly suitable moisturizers have n in the range of 4 to 600; and when R=CH$_3$, particularly suitable moisturizers have n in the range of 2 to 34. The optional polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether. Furthermore, the ethoxylated nonyl phenols and ethoxylated octyl phenols, particularly nonoxynol, C$_9$H$_{19}$C$_6$H$_4$(OCH$_2$CH$_2$)$_n$—OH, wherein n averages at least 6 and up to about 100; and octoxynol, C$_8$H$_{17}$S$_6$H$_4$(OCH$_2$CH$_2$)$_n$—OH, wherein n averages at least 7 and up to about 40, also are suitable moisturizers for use in the composition of the present invention. Suitable ethoxylated fatty alcohols for use as moisturizers in the composition of the present invention include compounds having the formula R—(OCH$_2$CH$_2$)$_n$OH, wherein R is an alkyl group containing from about 12 to about 30 carbon atoms and n averages at least 6. In addition, fatty alcohol polyglycol ethers having the formula

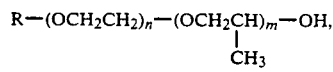

wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply without post-perm odor while providing a strong, tight curl and leaving the hair unexpectedly soft. The composition can be lotion or water wrapped and can be used with or without heat.

Four reducing agent-containing compositions were prepared containing cysteine and ammonium thioglycolate. It is understood that cysteine performs the same reducing agent function as its salts, such as the strong mineral acid salts, e.g., salts formed from phosphoric or sulfuric acids, and the like, e.g., cysteine hydrochloride.

Four reducing agent compositions of the present invention were prepared as follows:

| INGREDIENT | PERCENT BY WEIGHT |
|---|---|
| COMPOSITION 1 (pH:9.1) NORMAL HAIR | |
| WATER, DEIONIZED | 79.30% |
| AMMONIUM THIOGLYCOLATE (60%) | 10.00% |
| SODIUM HYDROXIDE (50%) | 1.50% |
| INCROMECTANT AQ (MOISTURIZER) | 1.00% |
| GLYCERIN USP | 2.00% |
| POLYSORBATE 20 (FRAGRANCE SOLUBILIZER) | .90% |

| INGREDIENT | PERCENT BY WEIGHT |
|---|---|
| FRAGRANCE | .30% |
| AMMONIUM HYDROXIDE (28%) to pH:9.1 | |
| L-CYSTEINE FREE BASE | 5.00% |
| | 100.00% |

COMMENTS: Excellent curl, no odor.

| COMPOSITION 2 (pH:8.8) NORMAL HAIR | |
|---|---|
| WATER, DEIONIZED | 81.47% |
| L-CYSTEINE FREE BASE | 5.00% |
| AMMONIUM THIOGLYCOLATE (60%) | 8.33% |
| AMMONIUM BICARBONATE | 2.00% |
| IGEPAL CO-730 (FRAGRANCE SOLUBILIZER) | 0.90% |
| FRAGRANCE | 0.30% |
| INCROMECTANT AQ (MOISTURIZER) | 2.00% |
| AMMONIUM HYDROXIDE to pH:8.8 | |
| | 100.00% |

COMMENTS: Excellent curl, no odor.

| COMPOSITION 3 (pH:7.5) BLEACHED HAIR | |
|---|---|
| WATER, DEIONIZED | 84.30% |
| AMMONIUM THIOGLYCOLATE (60%) | 7.50% |
| AMMONIUM BICARBONATE | 2.00% |
| INCROMECTANT AQ (MOISTURIZER) | 1.00% |
| GLYCERIN USP | 2.00% |
| POLYSORBATE 20 (FRAGRANCE SOLUBILIZER) | 0.90% |
| FRAGRANCE | 0.30% |
| AMMONIUM HYDROXIDE (28%) to pH:7.5 | |
| L-CYSTEINE FREE BASE | 2.00% |
| | 100.00% |

COMMENTS: Excellent curl, no odor.

| COMPOSITION 4 (pH:9.5) RESISTANT HAIR | |
|---|---|
| WATER, DEIONIZED | 77.45% |
| AMMONIUM THIOGLYCOLATE (60%) | 10.85% |
| SODIUM HYDROXIDE (50%) | 1.50% |
| INCROMECTANT AQ (MOISTURIZER) | 1.00% |
| GLYCERIN USP | 2.00% |
| POLYSORBATE 20 (FRAGRANCE SOLUBILIZER) | 0.90% |
| FRAGRANCE | 0.30% |
| AMMONIUM HYDROXIDE (28%) to pH:9.5 | |
| L-CYSTEINE FREE BASE | 6.00% |
| | 100.00% |

COMMENTS: Excellent curl, no odor.

The reducing agent-containing Composition 1 was test applied to heads of hair in the Helene Curtis, Inc. Salon Testing Center. The reducing agent Composition 1 was oxidized with a hydrogen peroxide-based neutralizer. None of the test subjects commenting on the permanent wave composition noticed any post-perm odor and all subjects were very pleased with the soft, natural feel left in the hair. Similarly, compositions 2, 3 and 4 leave no post-perm odor in the hair.

The following prior art composition 5, as disclosed in U.S. Pat. No. 4,913,900, produces an excellent curl, but leaves the hair with a strong post-perm odor:

| COMPOSITION 5 (pH:8.4) PRIOR ART | |
|---|---|
| WATER, DEIONIZED | 69.40% |
| AMMONIUM THIOGLYCOLATE (60%) | 22.90% |
| DIAMMONIUM DITHIODIGLYCOLATE (40%) | 1.00% |
| AMMONIUM HYDROXIDE (28%) to pH:8.4 | |
| AMMONIUM BICARBONATE | 2.00% |
| GLYCERIN USP | 3.50% |
| POLYSORBATE 20 (FRAGRANCE SOLUBILIZER) | 0.90% |
| FRAGRANCE | 0.30% |
| | 100.00% |

COMMENTS: Excellent curl, strong odor.

The following composition 6, containing too little thioglycolate did not leave the hair with a post-perm odor, but provided very poor curl:

| COMPOSITION 6 (pH:9.2) | |
|---|---|
| INGREDIENT | PERCENT BY WEIGHT |
| WATER, DEIONIZED | 79.75% |
| L-CYSTEINE | 5.00% |
| EDTA | 0.10% |
| AMMONIUM THIOGLYCOLATE (50%) | 2.00% |
| MONOETHANOLAMINE (pH) | 3.00% |
| AMMONIUM HYDROXIDE (28%) to pH:9.2 | |
| EMACOL X-606E (CONDITIONER) | 10.00% |
| PERFUME HC-2221-H | 0.06% |
| LATEX E-308 (OPACIFIER) | 0.05% |
| D & C YELLOW #10 (2%) | 0.04% |
| | 100.00% |

COMMENTS: Little to no curl, no odor

Obviously, many modifications and variations of the invention as hereinbefore set forth can be made without departing from the spirit and scope thereof and therefore only such limitations should be imposed as are indicated by the appended claims.

What is claimed is:

1. A composition capable of breaking sulfur to sulfur bonds in human hair for permanently waving hair when in contact with said human hair so that said hair can be reconfigured in a predetermined configuration substantially without generating odor, consisting of an aqueous solution of a cysteine free base in an amount of about 2.0% to about 6.5% by weight; an alkaline thioglycolate in an amount of about 3.5% to about 8.0% by weight; and sufficient alkali such that the composition has a pH of about 7.5 to about 9.5.

2. The composition of claim 1, wherein the cysteine is present in the composition in an amount of about 4.0% to about 6.0% by weight of the composition; the thioglycolate is present in the composition in an amount of about 5.0% to about 7.0% by weight of the composition; and the composition has a pH in the range of about 9.0 to about 9.5.

3. The composition of claim 1, wherein the cysteine is included in an amount of about 5.0% to about 6.5% by weight of the composition; wherein the alkaline thioglycolate is included in an amount of about 5.5% to about 7.5% by weight of the composition and the pH is in the range of about 9.0 to about 9.5.

4. The composition of claim 1, wherein the cysteine is included in an amount of about 2.0% to about 4.0% by weight of the composition; wherein the alkaline thioglycolate is included in an amount of about 3.5% to about 5.5% by weight of the composition, and the pH is in the range of about 7.5 to about 8.5.

5. The composition of claim 1 further including a polyhydric moisturizer in an amount of about 0.1% to about 20% by weight of the composition, and wherein the polyhydric moisturizer is selected from the group consisting of polyhydroxyalkyl compounds; polyalkylene glycols; glyceryl ether compounds; ethoxylated fatty alcohols; ethoxylated alkyl phenols; fatty alcohol polyglycol ether compounds; and mixtures thereof.

6. The composition of claim 1, wherein the alkaline thioglycolate is ammonium thioglycolate.

7. The composition of claim 2, wherein the alkaline thioglycolate is ammonium thioglycolate.

8. The composition of claim 3, wherein the alkaline thioglycolate is ammonium thioglycolate.

9. The composition of claim 4, wherein the alkaline thioglycolate is ammonium thioglycolate.

10. The composition of claim 1 further including a conditioning agent selected from the group consisting of a silicone and a polymeric quaternary ammonium compound, in an amount of about 0.1% to about 20% by weight of the composition.

11. A composition capable of breaking sulfur to sulfur bonds in human hair for permanently waving hair when in contact with said human hair so that said hair can be reconfigured in a predetermined configuration, consisting of an aqueous solution of a cysteine free base in an amount of about 2.0% to about 6.5% by weight; an alkaline thioglycolate in an amount of about 4.5% to about 8.0% by weight; and sufficient alkali such that the composition has a pH in the range of about 7.5 to about 9.5.

12. The composition of claim 11 further including a polyhydric moisturizer in an amount of about 0.1% to about 20% by weight of the composition, and wherein the polyhydric moisturizer is selected from the group consisting of polyhydroxyalkyl compounds; polyalkylene glycols; glyceryl ether compounds; ethoxylated fatty alcohols; ethoxylated alkyl phenols; fatty alcohol polyglycol ether compounds; and mixtures thereof.

13. The composition of claim 12, wherein the cysteine is present in the composition in an amount of about 4.0% to about 6.0% by weight of the composition; the thioglycolate is present in the composition in the amount of about 5.0% to about 7.0% by weight of the composition; and the composition has a pH in the range of about 9.0 to about 9.5.

14. The composition of claim 12, wherein the cysteine is included in an amount of about 5.0% to about 6.5% by weight of the composition; wherein the alkaline thioglycolate is included in an amount of about 5.5% to about 7.5% by weight of the composition, and the pH is in the range of about 9.0 to about 9.5.

15. The composition of claim 12, wherein the cysteine is included in an amount of about 2.0% to about 4.0% by weight of the composition; wherein the alkaline thioglycolate is included in an amount of about 4.5% to about 5.5% by weight of the composition, and the pH is in the range of about 7.5 to about 8.5.

16. A method of breaking sulfur to sulfur bonds in human hair to leave the hair weakened so that it can be reconfigured to a predetermined configuration, including contacting the hair with an aqueous reducing agent-containing composition consisting of about 2.0% to about 6.5% by weight of a cysteine free base; about 3.5% to about 8.0% of an alkaline thioglycolate; and sufficient alkali such that the composition has a pH of about 7.5 to about 9.5; forming the hair in a desired configuration such that the hair is in contact with the reducing agent-containing composition for a predetermined amount of time while formed in the new configuration; and then removing most of the reducing agent-containing composition from the hair at the expiration of the predetermined time period.

17. The method of claim 16, further including wrapping a plurality of human hair sections around a plurality of mandrels to reconfigure the hair sections in a plurality of curl configurations such that the hair is curl-configured while in contact with the reducing agent-containing composition; and removing the mandrels sequentially after said predetermined time period without testing the hair from one of the first removed mandrels for curl tightness.

18. The method of claim 16, wherein the cysteine is present in the composition in an amount of about 4.0% to about 6.0% by weight of the composition; the thioglycolate is present in the composition in an amount of about 5.0% to about 7.0% by weight of the composition; and the composition has a pH in the range of about 9.0 to about 9.5.

19. The method of claim 16, wherein the cysteine is included in an amount of about 5.0% to about 6.5% by weight of the composition; wherein the alkaline thioglycolate is included in an amount of about 5.5% to about 7.5% by weight of the composition, and the pH is in the range of about 9.0 to about 9.5.

20. The method of claim 16, wherein the cysteine is included in an amount of about 2.0% to about 4.0% by weight of the composition; wherein the alkaline thioglycolate is included in an amount of about 3.5% to about 5.5% by weight of the composition, and the pH is in the range of about 7.5 to about 8.5.

* * * * *